US007486398B1

(12) United States Patent
Cole

(10) Patent No.: US 7,486,398 B1
(45) Date of Patent: Feb. 3, 2009

(54) GROUNDWATER MONITORING SYSTEM AND METHOD

(75) Inventor: Barrett E. Cole, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/026,320

(22) Filed: Feb. 5, 2008

(51) Int. Cl.
 *G01N 21/00* (2006.01)
(52) U.S. Cl. ...................................... 356/436; 356/432
(58) Field of Classification Search ........................ None
 See application file for complete search history.

(56) References Cited

U.S. PATENT DOCUMENTS

| | | | |
|---|---|---|---|
| 4,669,536 A | 6/1987 | Ames et al. ................... 166/72 |
| 5,059,790 A * | 10/1991 | Klainer et al. ......... 250/227.21 |
| 5,116,759 A * | 5/1992 | Klainer et al. ........... 435/287.2 |
| 5,268,972 A | 12/1993 | Tabacco et al. ................ 385/2 |
| 5,922,975 A | 7/1999 | Butler et al. ............. 73/864.74 |
| 6,021,664 A | 2/2000 | Granato et al. ............. 73/53.01 |
| 6,357,969 B1 | 3/2002 | Wheeler, Jr. et al. ........ 405/274 |
| 2007/0007005 A1 | 1/2007 | Heller et al. ........... 166/250.01 |

FOREIGN PATENT DOCUMENTS

WO  WO 2007/008844 A2  1/2007
WO  WO 2007/008844 A3  1/2007

\* cited by examiner

*Primary Examiner*—Michael P Stafira
(74) *Attorney, Agent, or Firm*—Kris T. Fredrick; Kermit D. Lopez; Luis M. Ortiz

(57) ABSTRACT

A system and method for monitoring toxic chemicals in groundwater includes the use of a groundwater vaporizer and a CRDS (Cavity Ring Down Spectroscopy) block. The CRDS block includes a three-mirror ring down cavity in which a fiber is coupled to a top prismatic mirror in order to permit vertical entry of a laser beam. One of the mirrors can be piezo-electrically tuned so that the ring down cavity is in resonance with the laser beam and a third mirror includes a read out detector to measure the laser beam intensity. Vapors from the groundwater vaporizer pass through vapor inlet channels, which include a permeable membrane in order to permit vapors to flow into the ring down cavity. The system monitors, for example, trichloroethylene (TCE) concentrations and other chemicals present in groundwater utilizing data transmitted from the read out detector.

23 Claims, 9 Drawing Sheets

GROUNDWATER MONITORING SYSTEM AND METHOD

TECHNICAL FIELD

Embodiments are generally related to groundwater monitoring methods and systems. Embodiments are also related to the optical detection of toxic chemicals in groundwater.

BACKGROUND OF THE INVENTION

Effective groundwater management can protect the quantity of groundwater and ensure a dependable and affordable supply of groundwater into perpetuity. Proper groundwater supervision and monitoring can also protect water quality to ensure that the groundwater remains suitable for domestic, industrial, agricultural, and environmental uses. Additionally, proper groundwater management seeks to prevent land subsidence, which can damage expensive public and private infrastructure such as, for example, water conveyance, flood control facilities, and water wells. Various contaminants and toxic chemicals can be found in groundwater, such as volatile organic compounds, nonvolatile materials, metal contaminants, and the like. These contaminants can exist in subsurface soil and groundwater in a liquid or vapor phase as discrete substances and may be mixed with and/or dissolved in groundwater and soil gases.

Groundwater monitoring can be utilized for detecting the presence of toxic chemicals and other contaminants in groundwater. Such monitoring typically involves measuring physical and/or chemical properties of groundwater on a periodic basis. Concentrations of the contaminants can be frequently monitored to determine if the concentrations are increasing, decreasing, or remaining in approximately the same range. Monitoring can also be performed at and/or in the vicinity of water supply sources to determine the quality of water.

Groundwater monitoring is typically accomplished by sinking wells and then drawing a number of samples at different locations from the well for lab analysis. Taking water from the well to analyze and distribute the flow in the well must be performed carefully in order to ensure that the sample is a faithful representation of the groundwater. Manual methods have traditionally been utilized for groundwater monitoring. In each of these manual methods, the well must be re-pumped frequently in order to draw a number of groundwater samples, which is a time-consuming and inefficient process.

Sensors such as, for example, MIPS (Membrane Interface Probe Sensors) can be located down a well. Such devices, however, tend to be less sensitive than desired in order to measure toxic chemicals such as trichloroethylene (TCE) below the carcinogenic levels of 5 ppb (parts per billion). The size of the sensors, pressure transducers and other probes utilized by prior art groundwater monitoring systems also limits the minimum diameter of the well in which they are installed.

In an effort to address the foregoing difficulties, it is believed that a need exists for an improved system and method for detecting and monitoring toxic chemical contaminants in groundwater as disclosed in further detail herein.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved groundwater monitoring system and method.

It is another aspect of the present invention to provide for an improved method and system for monitoring toxic chemicals in groundwater utilizing CRDS (Cavity Ring Down Spectroscopy).

The aforementioned aspects and other objectives and advantages can now be achieved as described herein. A system and method is disclosed for monitoring toxic chemicals in groundwater. Such an approach includes the use of a groundwater vaporizer and a CRDS block. The CRDS block can be configured to include a three-mirror ring down cavity in which a fiber is coupled to a top prismatic mirror in order to permit vertical entry of a laser beam. One of the mirrors can be piezo-electrically tuned so that the ring down cavity is in resonance with the laser beam and a third mirror. A read-out detector can be utilized to measure the laser beam intensity. Vapors from the groundwater vaporizer pass through vapor inlet channels, which include a permeable membrane in order to permit vapors to flow into the ring down cavity. Such a system can be utilized to monitor, for example, trichloroethylene (TCE) concentrations and other chemicals present in the groundwater utilizing the data sent out from the read-out detector.

The permeable membrane can be utilized to seal holes in the ring down cavity, while permitting vapors from the groundwater vaporizer to flow into the cavity, which prevents the groundwater sample from entering the cavity. The CRDS block is sensitive to two partial pressures because of the long path length in order to ensure that a reliable and accurate measure of groundwater constituents can be attained. The aforementioned mirrors can be heated in order to avoid condensation on the mirrors during a measurement operation. The laser beam can be pumped through the optical fiber that extends to a well top. The tunable laser can be utilized to interrogate the three-mirror cavity and provide a measure of the TCE concentrations and other toxic chemicals in the groundwater.

The CRDS block can be placed in the well and the laser can be moved from block to block throughout the well in order to sample different units. The three-mirror cavity configuration described herein enables measurements at wavelengths of SWIR (Short-wave Infrared) bands in order to provide an identification of the material and a measure of concentration of toxic chemicals in the vapors of the groundwater. The groundwater concentration can be back calculated by knowing the temperature of the groundwater utilizing the well-known Henry's law.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
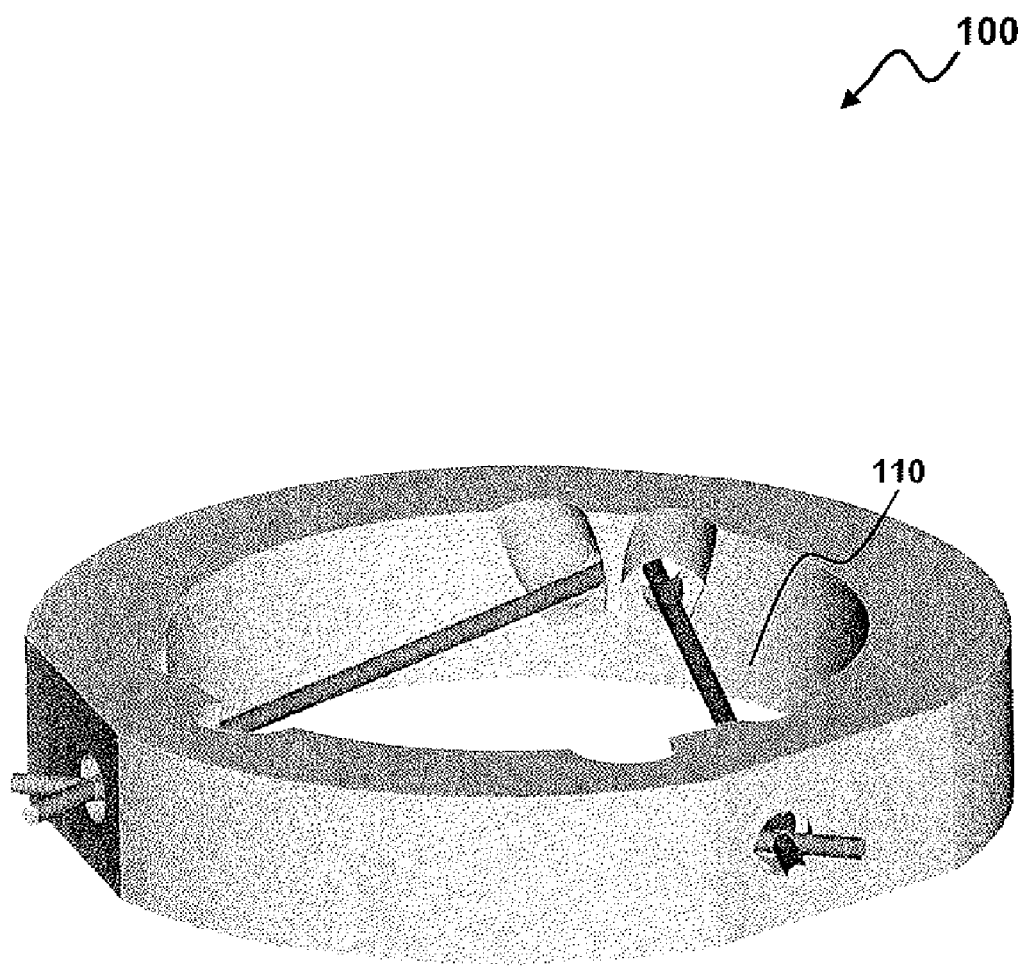
FIG. 1 illustrates a perspective view of a CRDS block for high sensitivity gas sensing, which can be adapted for use in implementing a preferred embodiment.

Referring to FIG. 1, a perspective view of a CRDS block 100 for high sensitivity gas sensing is illustrated, which can be adapted for use in implementing a preferred embodiment. The CRDS block 100 (e.g., a CRDS block) can be utilized to measure the concentration of a light-absorbing substance, where the CRDS is a form of laser absorption spectroscopy. The CDRS component 100 generally constitutes a ring-down cavity 110 that refers to the space between at least two mirrors facing each other. CRDS records the absorption spectrum of a species or sample inside the ring-down cavity 110 (i.e., a CRDS cavity) by measuring the change in the ring-down lifetime as a function of wavelength. The ring-down cavity 110 can be provided that is capable of supporting a ring-down event. Optical cavities capable of supporting a ring-down event include cavities provided by for instance input/output couplers, mirrors, gratings or reflectors. Furthermore, optical cavities include linear optical cavities as well as other non-linear types such as ring cavities, bow-tie cavities, litman cavities, or other suitable cavities, to include fiber optics or other light-guiding materials, within which ring-down can be observed.

Figure 2:
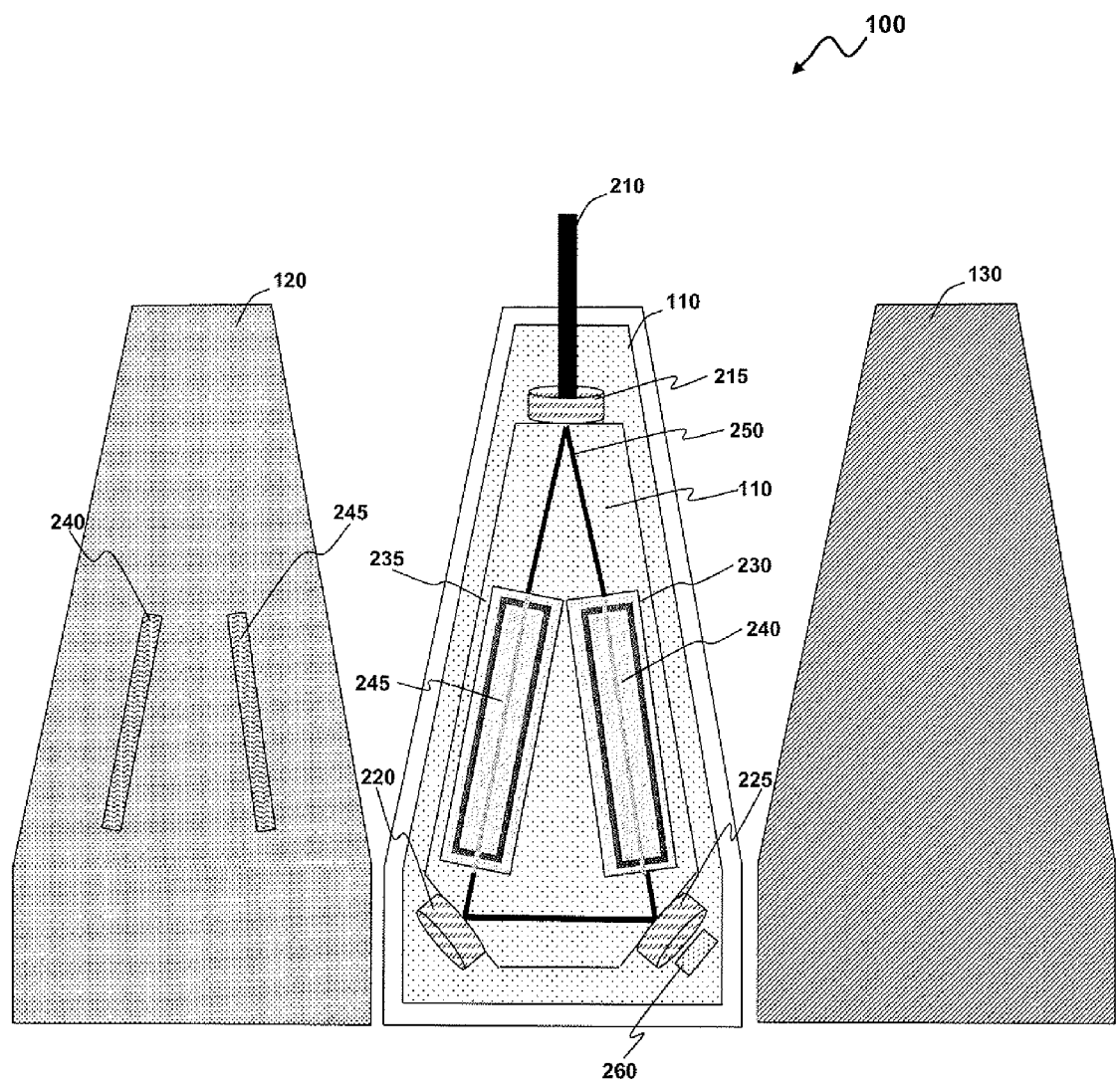
FIG. 2 illustrates an exploded front view of a CRDS block for monitoring toxic chemicals in groundwater, which can be implemented in accordance with a preferred embodiment.

Referring to FIG. 2, an exploded front view of the CRDS block 100 depicted in FIG. 1 is shown in greater detail, in accordance with a preferred embodiment. Note that in FIGS. 1-9, identical or similar parts or elements are generally disclosed by the same reference numerals. The CRDS block 100 generally includes an upper block 130, a lower block 120 and the CRDS cavity 110. The CRDS cavity 110 can be configured to include three mirrors 215, 220 and 225, which are arranged in a triangular fashion in order to capture a laser beam 250 in a polarized manner. An optical fiber 210 can be coupled to a first top prismatic mirror 215, which permits vertical entry of the laser beam 250 and coupling it into the CRDS cavity 110. The laser beam 250 can be utilized to directly detect molecular absorption at specific wavelengths.

The top prismatic entry mirror 215 can be adapted for splitting the incoming laser beam 250 in order to allow the laser beam 250 to pass through vapor inlet channels 240 and 245. The vapor inlet channels 240 and 245 include a vapor membrane 230 and 235, which can be provided as a permeable membrane configured from a material, such as, for example, Gore-Tex®. Note that Gore-Tex® represents just one of many different possible types of material that can be adapted for use in accordance with varying embodiments, and is discussed herein merely for general exemplary and illustrative purposes only and is not considered a limiting feature of the disclosed embodiments.

The vapor from the groundwater passes through the vapor inlet channels 240 and 245 in the lower block 120. The vapor membrane 230 and 235 can be equipped for permitting vapor to flow into the CRDS cavity 110 and prevents groundwater sample from entering the CRDS cavity 110. One of the mirrors 215, 220 and 225 can be piezo-electrically tuned so that the CRDS cavity 110 can be made in resonance with the laser beam 250 entering from the optical fiber 210. The laser beam 250 passing through the vapor inlet channels 240 and 245 can be correlated with the groundwater vapors. The third mirror 225 includes a read out detector 260 to detect the laser beam 120 exiting the CRDS cavity 110, which provides an identification of toxic chemicals and measure of concentration of the chemicals. The temperature of the groundwater can be utilized to calculate the concentration of toxic chemicals utilizing Henry's law. The mirrors 215, 220 and 225 can be heated in order to avoid condensation on the mirrors 215, 220 and 225 during the measurements.

Figure 3:
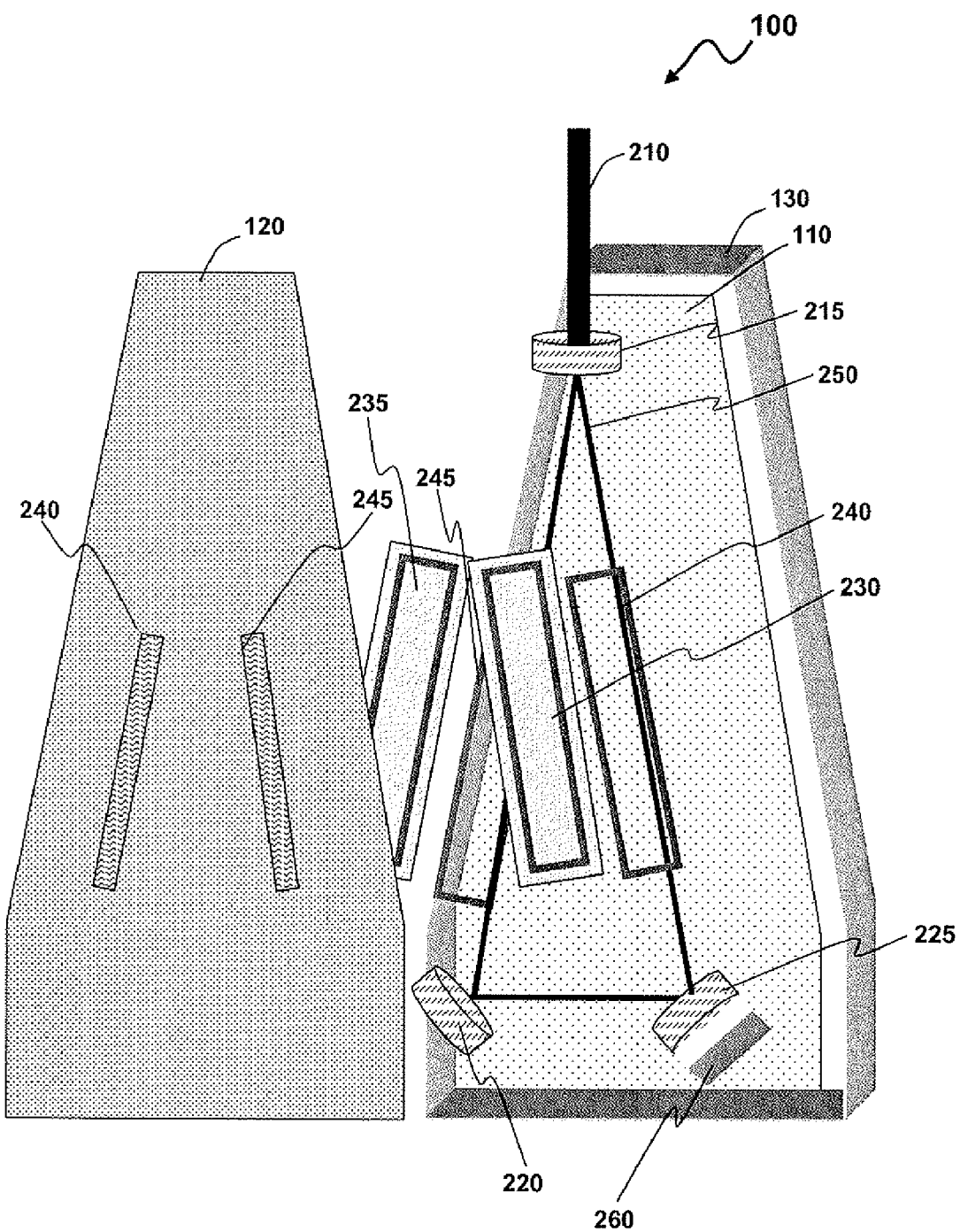
FIG. 3 illustrates a perspective view of the a component for monitoring toxic chemicals in groundwater, which can be implemented in accordance with a preferred embodiment.

Referring to FIG. 3, a perspective view of the CRDS block 100 for monitoring groundwater is illustrated, which can be implemented in accordance with a preferred embodiment. A laser beam 250 can be injected into the CRDS cavity 110, and bounces back and forth between the mirrors 215, 220 and 225, losing some intensity at each reflection. The CRDS cavity 110 produces an exponentially growing ring-up beam with a ring-up rate when the laser beam 250 is injected and produces an exponentially decaying ring-down beam with a decay rate when the laser beam 250 is interrupted with vapors of groundwater. The read out detector 240 can be utilized to measure and/or detect the ring-down time or light intensity depending on the operation of the cavity 110 either in decay mode or in intensity mode.

Figure 4:
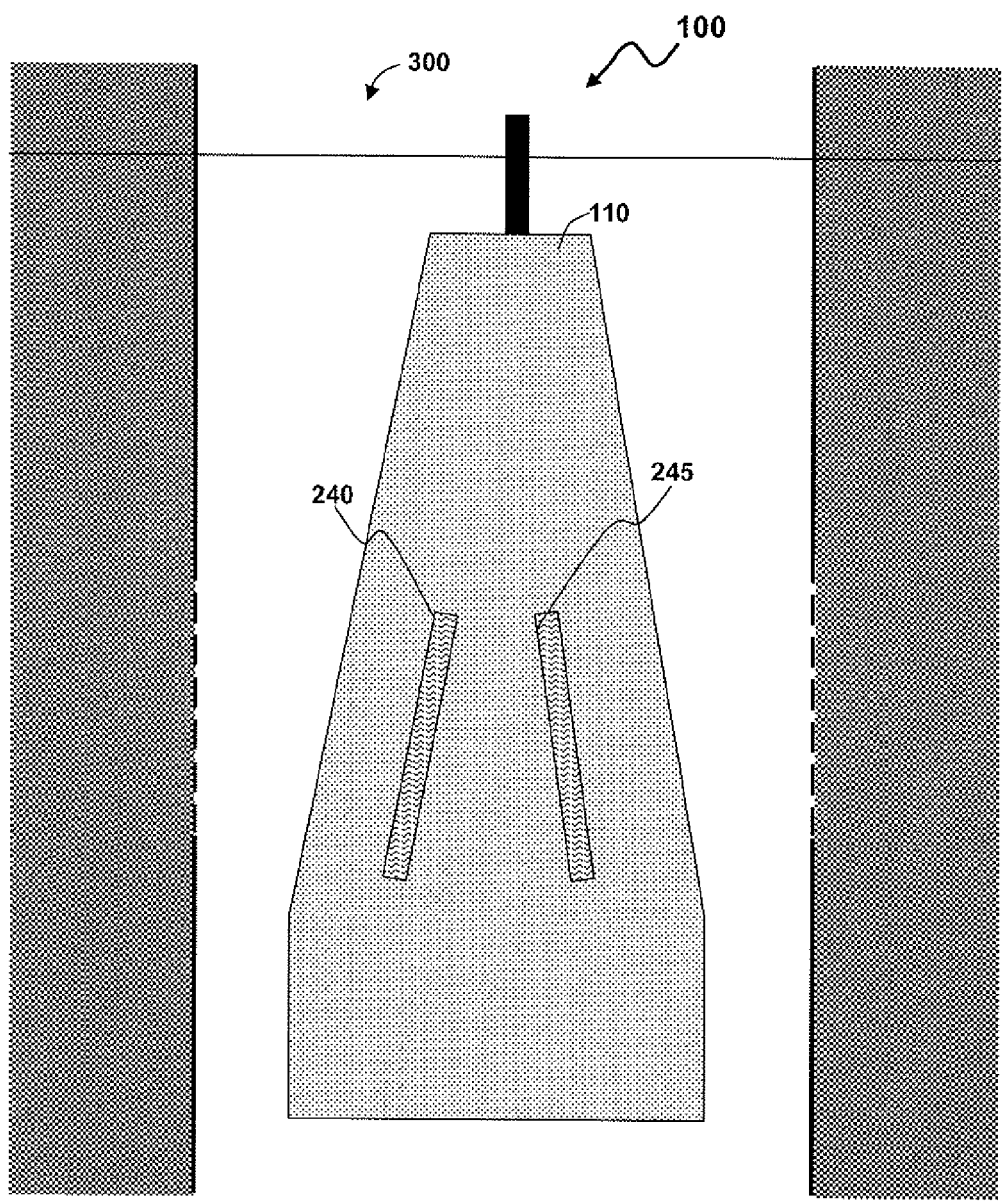
FIG. 4 illustrates an assembled view of a CRDS block for monitoring toxic chemicals in groundwater, which can be implemented in accordance with a preferred embodiment.

Referring to FIG. 4, an assembled view of the CRDS block 100 for monitoring groundwater is illustrated, in accordance with a preferred embodiment. The CRDS block 110 can be placed in a well 300 as shown in FIG. 4 and the laser beam 250 can be moved from block to block throughout the well 300 in order to sample different units.

Figure 5:
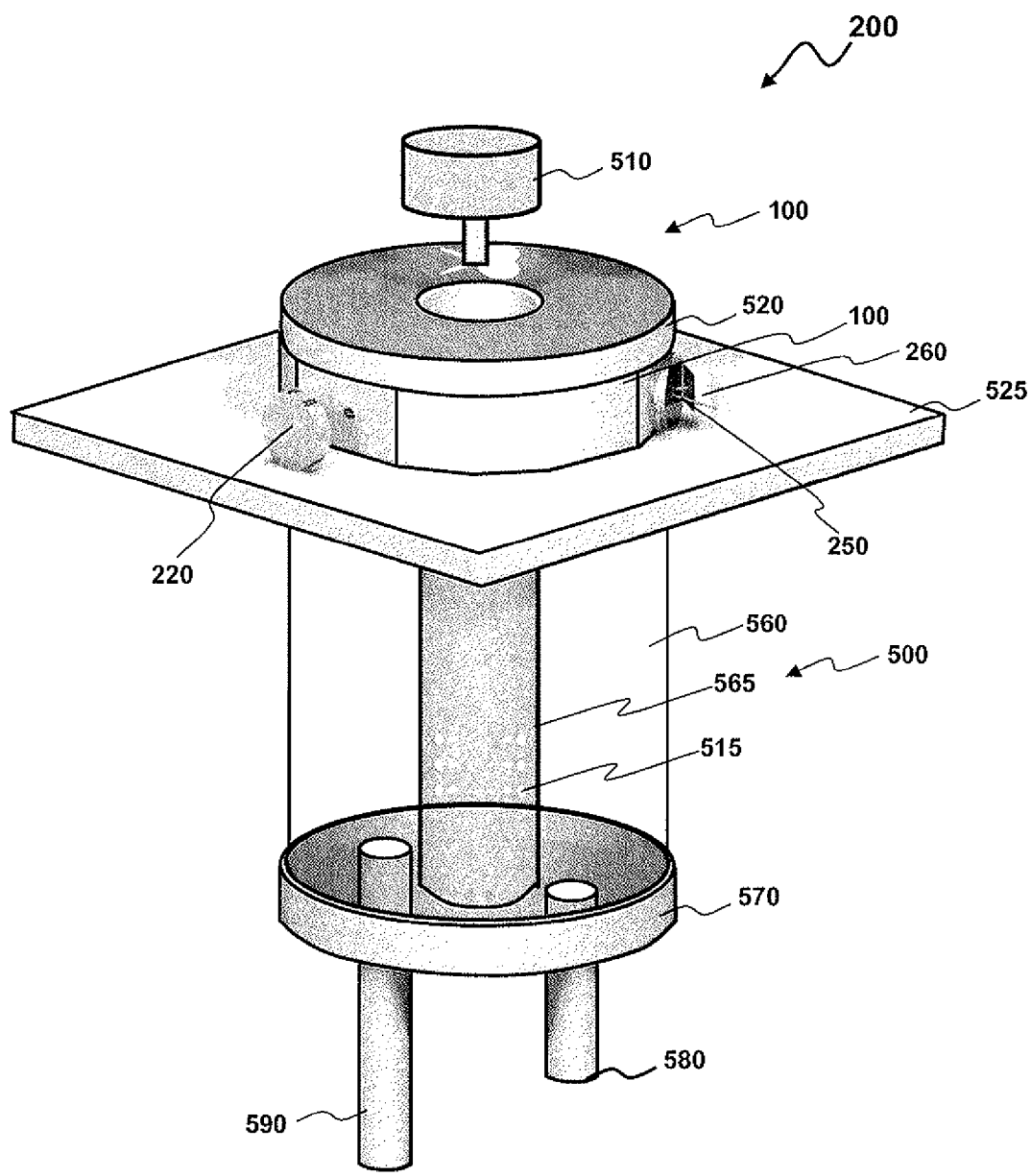
FIG. 5 illustrates a perspective view of a CRDS groundwater monitoring system for monitoring toxic chemicals in groundwater, which can be implemented in accordance with a preferred embodiment.

Referring to FIG. 5, a perspective view of CRDS groundwater-monitoring system 200 for monitoring toxic chemicals in groundwater is illustrated, which can be implemented in accordance with a preferred embodiment. The CRDS groundwater monitoring system 200 can be utilized for monitoring toxic chemicals present in the groundwater from the well 300 at regular intervals. The CRDS groundwater monitoring system 200 generally includes a groundwater vaporizer 500 and the CRDS block 100 for measuring and analyzing the vapors of groundwater from the well 300 by injecting the vapors of groundwater sample into the CRDS cavity 110.

The CRDS groundwater monitoring system 200 also includes, for example, a vapor transport fan 510 and a copper lid or heat conductor 520 for covering the CRDS cavity 110. The copper lid or heat conductor 520 can be welded to the top of the CRDS cavity 110. The groundwater vaporizer 500 includes an internal water wick 565 enclosed by an outer vapor container 560 of finite length which is equipped with an aquifer inlet port 590 and an overflow port 580 for supplying or refilling the outer vapor container 560 with vapor from the groundwater source. The internal water wick 565 preferably includes slots 515, screens or some other type of openings to allow for the intake of vapors from the outer vapor container 560.

Figure 6:
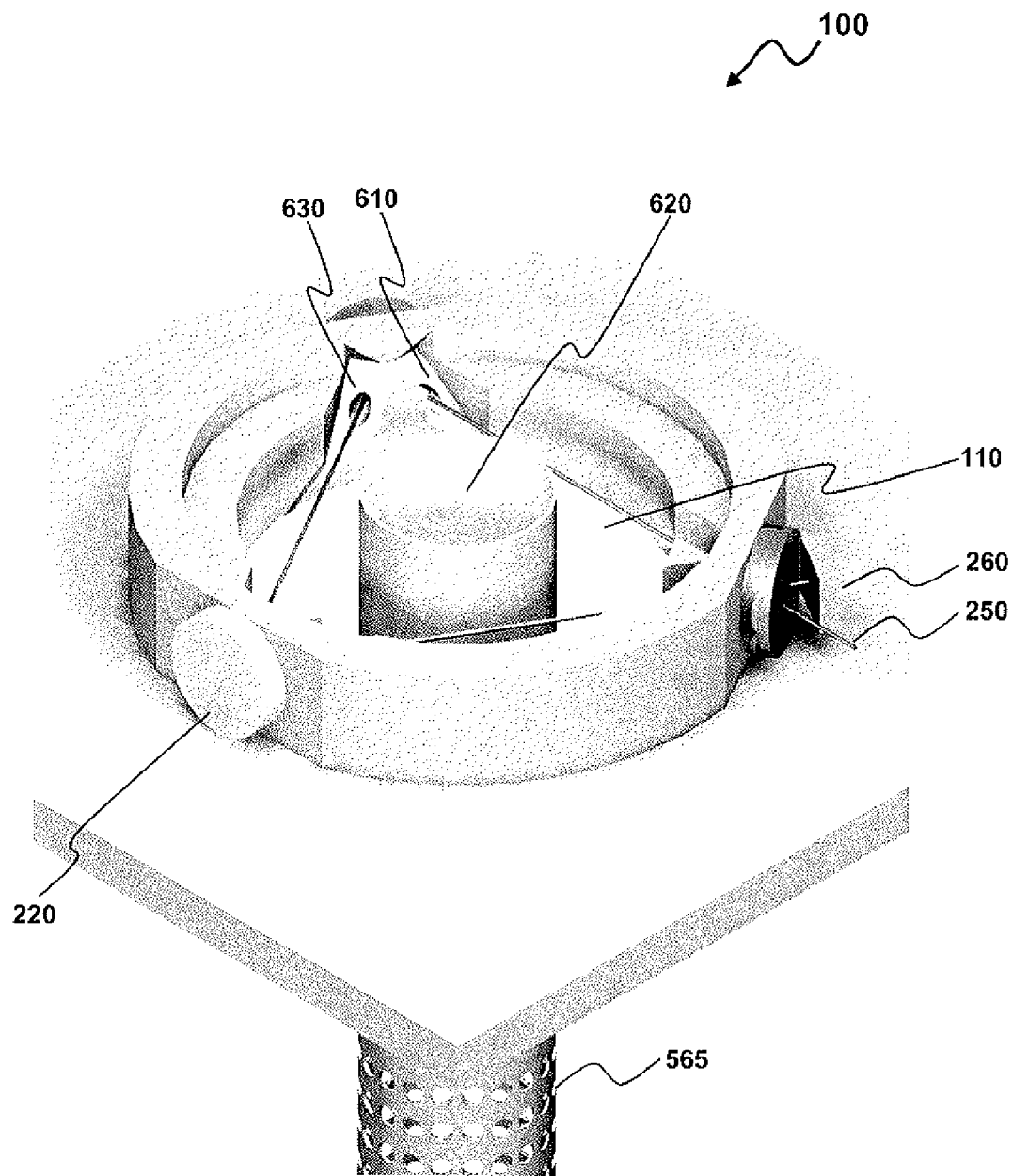
FIG. 6 illustrates an exploded top view of a CRDS block for monitoring toxic chemicals in groundwater, which can be implemented in accordance with a preferred embodiment.

Referring to FIG. 6, a top view of the CRDS block 100 for monitoring groundwater is illustrated, which can be implemented in accordance with a preferred embodiment. A Brewster window 130 is adapted for providing mirror protection to the mirrors 215, 220 and 225 in the CRDS cavity 110. The CRDS cavity 110 includes a central vapor transport channel 620 and is utilized for transportation of vapors from the groundwater vaporizer 500.

Figure 7:
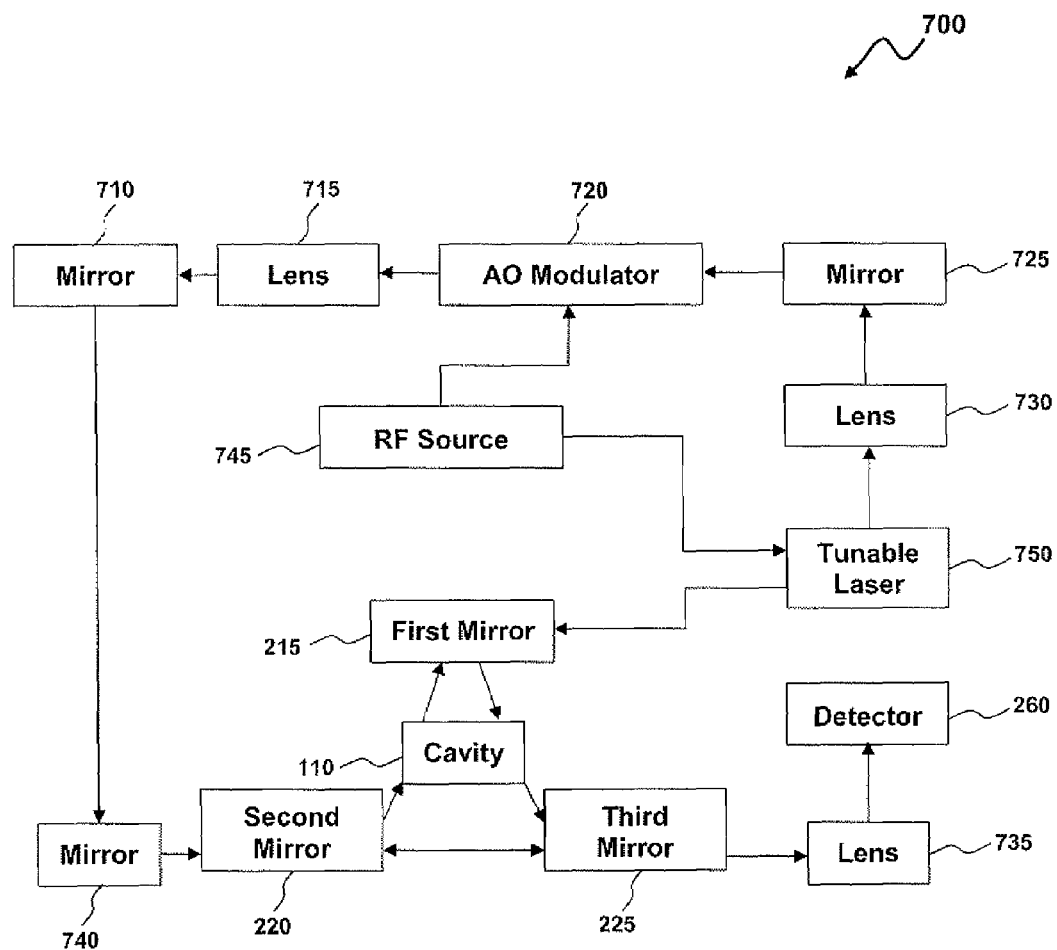
FIG. 7 illustrates a block diagram showing major components of the CRDS groundwater monitoring system, which can be implemented in accordance with an alternative embodiment.

Referring to FIG. 7, a block diagram showing major components of the CRDS groundwater monitoring system 700 is illustrated, which can be implemented in accordance with an alternative embodiment. The CRDS groundwater monitoring system 700 includes a radio frequency (RF) source 745, which is coupled to a tunable laser 750 and an acousto-optic (AO) modulator 720. The wavelength of the tunable laser 502 can be altered in a controlled manner. The tunable laser 750 generates the laser beam 250 that can be guided by a mirror 725 via a lens 730. The mirror 725 reflects the laser beam 250 to pass into the AO modulator 720 without any distortion loss.

The AO modulator 720 is capable of splitting the laser beam 250 into a plurality of modes having a relative frequency offset. The AO modulator 720 passes the laser beam 120 to another optics 715, which may include a number of elements but generally comprises a focusing lens. Additional mirrors 710 and 740 can be optionally provided to reflect the laser beam 250 from the AO modulator 720 to the CRDS cavity 110. The CRDS cavity 110 includes three mirrors 215, 220 and 225, where the laser beam 250 can be passed through the optical fiber 210 as shown in FIG. 2 to the first mirror 215. The laser beam 250 is abruptly shut off by the AO modulator 720 when sufficient light buildup is achieved inside the ring-down cavity 110.

The laser beam 120 resonates between the mirrors 215, 220 and 225 inside the ring-down cavity 110. The intensity of the laser beam 250 will decrease by a fixed percentage due to both absorption and reflectivity losses. The intensity of light within the cavity 110 can then be determined as an exponential function of time. The resonated laser beam 250 can be coupled to the detector 260 through an optional lens 735. The detector 260 can be activated to detect the concentration of toxic chemicals in groundwater using the resonated laser beam 250. This arrangement provides a reliable and efficient monitoring and detection of toxic chemicals present in the groundwater from the well in a cost-effective manner.

Figure 8:
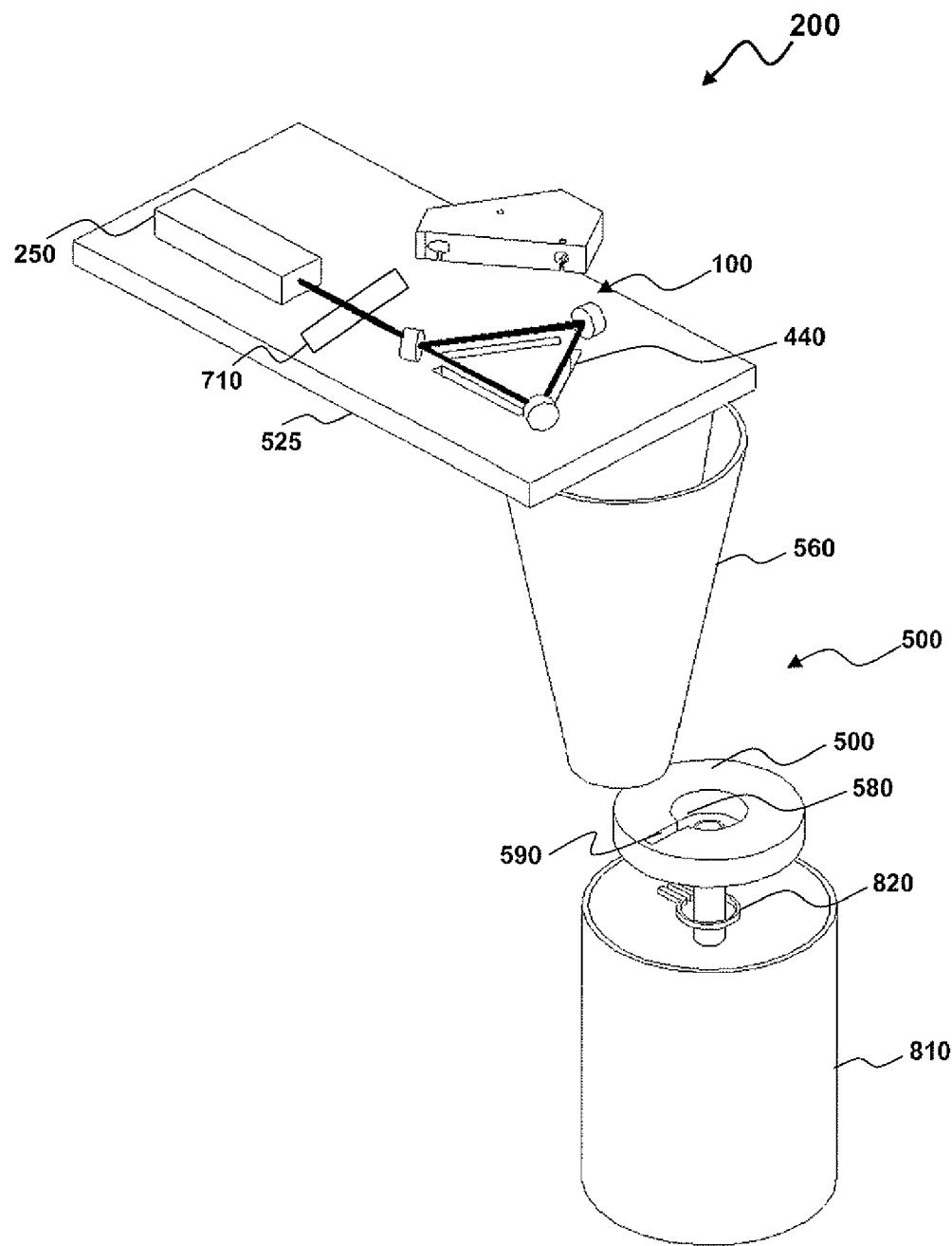
FIG. 8 illustrates a schematic view of the CRDS groundwater monitoring system for monitoring toxic chemicals in ground water, which can be implemented in accordance with a preferred embodiment.

Referring to FIG. 8 a schematic view of the CRDS groundwater-monitoring system 200 for monitoring ground water is illustrated, which can be implemented in accordance with a preferred embodiment. The groundwater vapor analyzer with CRDS block 100 can be placed on a well cap plate 525. The vapor inlet channels 240 and 245 of the CRDS block 100 can be directly overlaid on the outer membrane 560 of the wick manifold 565. The groundwater sample passes through a wellhead pipe 810 to the aquifer inlet 590, which is heated by a micro heater 820. The groundwater vapor analyzer 500 passes vapors of the groundwater sample to the CRDS block 100 in order to monitor toxic chemicals from the groundwater sample. The acousto-optic modulator 710 deflects light generated by the laser beam 250 into cavity 110 that allows relatively high in-coupling efficiencies.

Figure 9:
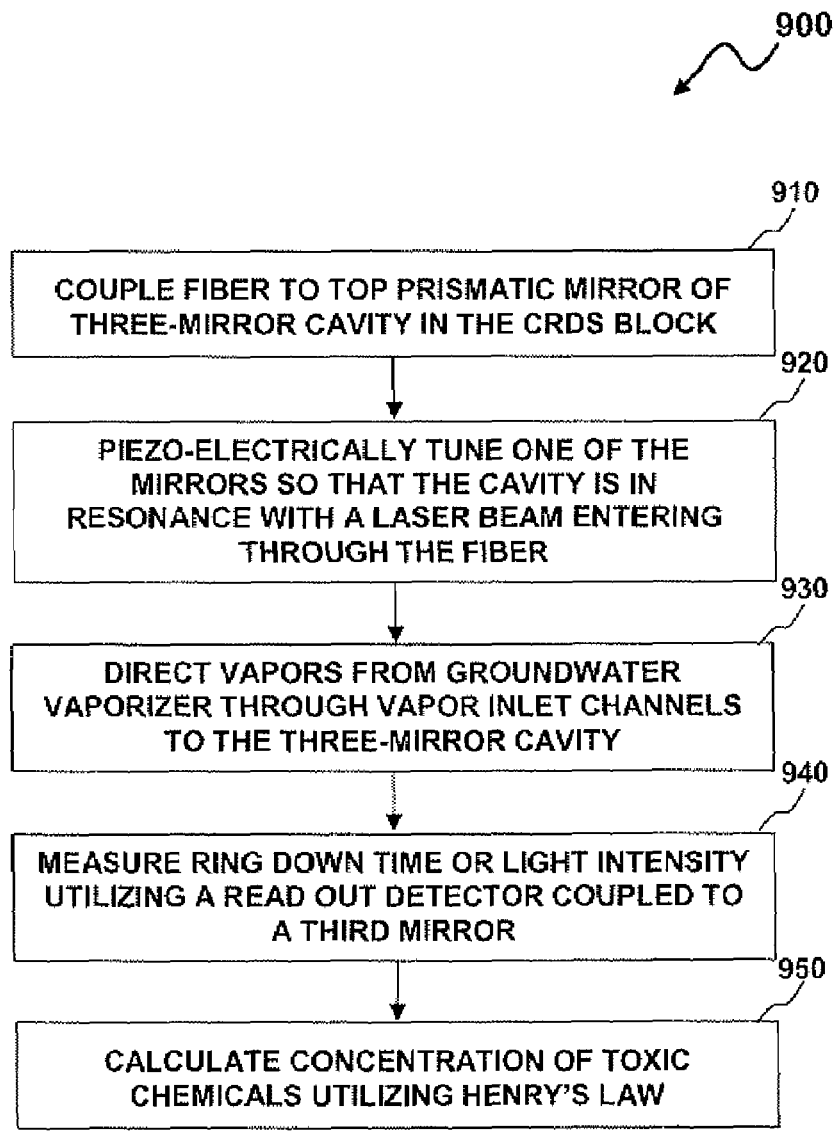
FIG. 9 illustrates a detailed flow chart of operations illustrating logical operational steps of a method for monitoring toxic chemicals in groundwater, in accordance with an alternative embodiment.

Referring to FIG. 9, a detailed flow chart of operations illustrating logical operational steps of a method 900 for monitoring toxic chemicals in groundwater is illustrated, in accordance with an alternative embodiment. The optical fiber 210 can be coupled to a top prismatic mirror 215 of a three-mirror cavity 110 in the CRDS block 100, as depicted at block 910. Thereafter, as indicated at block 920, one of the mirrors 215, 220 and 225 can be piezo-electrically tuned so that the cavity 110 is in resonance with a laser beam 250 entering from the optical fiber 210. The vapors from a groundwater vaporizer 500 can be directed through the vapor inlets channels 240 and 245 in the lower block 120 which includes a permeable membrane 230 and 235 to the three-mirror cavity 110, as shown at block 930. Next, as described at block 940, the ring down time or light intensity can be measured utilizing a read out detector 260 coupled to the third mirror 225. The concentration of toxic chemicals in groundwater can be calculated using Henry's law, as depicted at block 950.

The CRDS cavity 110 enables measurements at wavelengths of short-wave infrared (SWIR) bands in order to provide an identification of the material and a measure of concentration of toxic chemicals in groundwater. The SWIR band wavelengths are suitable to absorb the TCE contents in the groundwater. The groundwater-monitoring system 200 can fit into a well with a 2" diameter and can monitor the toxic chemical contaminants in the groundwater from the well at regular intervals without human intervention.

Based on the foregoing, it can be appreciated that various embodiments involving CRDS monitoring are disclosed herein. Two basic concepts are described herein. The first concept involves placing the device (e.g., see FIGS. 5-6) in the well, but not in the water, and then drawing water up from the well and vaporizing it in to the module. The second concept (e.g., see FIGS. 2-4) involves putting the device in the well with a permeable membrane and simply letting the vapor pass through the membrane into the cavity. In either case, a top laser can be utilized to transmit light into a fiber (e.g., see FIG. 9) and down the well into the module. Thus, different techniques can be provided for performing measurements with respect to FIGS. 2-4 and 5-6, 9, where the former involves a block that sits in the water in the well with the laser above the ground and the latter involves a block that sits on top of the well with the laser and vaporized air delivered to the system for use by a below-ground vaporizer that sits in the well, but not in the water.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A groundwater monitoring system, comprising:
   a CRDS block having a ring down cavity therein, said CRDS block associated with at least three mirrors wherein said ring down cavity is capable of optical communication with a light source through an optical fiber associated with a first top prismatic mirror of said at least three mirrors;
   a groundwater vaporizer for directing vapors from groundwater through at least one vapor inlet channel associated with said CRDS block which include at least one permeable membrane in order to permit vapors to flow into said ring down cavity; and a read-out detector associated with a third mirror of said at least three mirrors for detecting a ring down time and/or a light intensity of said light source and thereby provide an identification and a measure of a concentration of a plurality of toxic chemicals in said groundwater.

2. The system of claim 1 further comprising:
an acousto-optic modulator for deflecting light generated by said light source onto said ring down cavity, wherein said acoustic-optic modulator is associated with said read-out detector, said groundwater vaporizer and said CRDS block.

3. The system of claim 1 wherein at least one mirror of said at least three mirrors is piezo-electrically tuned so that said ring down cavity is capable of being in resonance with said light source entering from said optical fiber.

4. The system of claim 1, wherein said light source comprises a laser beam.

5. The system of claim 1 wherein said read-out detector detects TCE concentrations in groundwater.

6. The system of claim 1 wherein said permeable membrane permits vapors to flow into said ring down cavity thereby preventing groundwater from entering said ring down cavity.

7. The system of claim 1 wherein said ring down cavity comprises a Brewster window mirror protection component.

8. A groundwater monitoring system, comprising:
a CRDS block having a ring down cavity therein, said CRDS block associated with at least three mirrors wherein said ring down cavity is capable of optical communication with a light source through an optical fiber associated with a first top prismatic mirror of said at least three mirrors;
a groundwater vaporizer for directing vapors from groundwater through at least one vapor inlet channel associated with said CRDS block which include at least one permeable membrane in order to permit vapors to flow into said ring down cavity;
a read-out detector associated with a third mirror of said at least three mirrors for detecting a ring down time and/or a light intensity of said light source and thereby provide an identification and a measure of a concentration of a plurality of toxic chemicals in said groundwater; and
an acousto-optic modulator for deflecting light generated by said light source onto said ring down cavity, wherein said acoustic-optic modulator is associated with said read-out detector, said groundwater vaporizer and said CRDS block.

9. The system of claim 7, wherein at least one mirror of said at least three mirrors is piezo-electrically tuned so that ring down cavity is capable of being in resonance with said light source entering from said optical fiber.

10. The system of claim 7, wherein said light source comprises a laser beam.

11. The system of claim 7, wherein said read-out detector detects TCE concentrations in groundwater.

12. The system of claim 7, wherein said permeable membrane permits vapors to flow into said ring down cavity thereby preventing groundwater from entering said ring down cavity.

13. The system of claim 7, wherein said ring down cavity comprises a Brewster window mirror protection component.

14. A groundwater monitoring method, comprising:
configuring a CRDS block to include a ring down cavity therein;
associating said CRDS block with at least three mirrors wherein said ring down cavity is capable of optical communication with a light source through an optical fiber associated with a first top prismatic mirror of said at least three mirrors;
utilizing a groundwater vaporizer to direct vapors from groundwater through at least one vapor inlet channel associated with said CRDS block which include at least one permeable membrane in order to permit vapors to flow into said ring down cavity; and
detecting a ring down time and/or a light intensity of said light source utilizing a read-out detector associated with a third mirror of said at least three mirrors, thereby providing an identification and a measure of a concentration of a plurality of toxic chemicals in said groundwater.

15. The method of claim 14 further comprising:
utilizing an acousto-optic modulator to deflect light generated by said light source onto said ring down cavity, wherein said acoustic-optic modulator is associated with said read-out detector, said groundwater vaporizer and said CRDS block.

16. The method of claim 14 wherein at least one mirror of said at least three mirrors is piezo-electrically tuned so that said ring down cavity is capable of being in resonance with said light source entering from said optical fiber.

17. The method of claim 1, wherein said light source comprises a laser beam.

18. The method of claim 1 wherein said read-out detector detects TCE concentrations in groundwater.

19. The method of claim 1 wherein said permeable membrane permits vapors to flow into said ring down cavity thereby preventing groundwater from entering said ring down cavity.

20. The method of claim 1 wherein said ring down cavity comprises a Brewster window mirror protection component.

21. A groundwater monitoring method, comprising:
configuring a CRDS block to include a ring down cavity therein;
associating said CRDS block with at least three mirrors, wherein said ring down cavity is capable of optical communication with a light source through an optical fiber associated with a first top prismatic mirror of said at least three mirrors;
utilizing at least one vapor inlet channel associated with said CRDS block which include at least one permeable membrane in order to permit vapors to flow into said ring down cavity; and
detecting a ring down time and/or a light intensity of said light source utilizing a read-out detector associated with a third mirror of said at least three mirrors, thereby providing an identification and a measure of a concentration of a plurality of toxic chemicals in said groundwater.

22. The method of claim 21 further comprising:
utilizing an acousto-optic modulator to deflect light generated by said light source onto said ring down cavity, wherein said acoustic-optic modulator is associated with said read-out detector, said groundwater vaporizer and said CRDS block.

23. The method of claim 21 wherein at least one mirror of said at least three mirrors is piezo-electrically tuned so that said ring down cavity is capable of being in resonance with said light source entering from said optical fiber.

* * * * *